(12) United States Patent
Ciceri et al.

(10) Patent No.: US 7,112,435 B1
(45) Date of Patent: Sep. 26, 2006

(54) UNCOUPLING OF DNA INSERT PROPAGATION AND EXPRESSION OF PROTEIN FOR PHAGE DISPLAY

(75) Inventors: Pietro Ciceri, La Jolla, CA (US); Patrick Parvis Zarrinkar, San Diego, CA (US); Daniel Kelly Treiber, San Diego, CA (US); David J. Lockhart, Del Mar, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 505 days.

(21) Appl. No.: 10/214,654

(22) Filed: Aug. 7, 2002

(51) Int. Cl.
*C12N 15/62* (2006.01)
*C12Q 1/68* (2006.01)
*C12Q 1/70* (2006.01)
*C07H 21/04* (2006.01)

(52) U.S. Cl. .................. 435/320.1; 435/5; 435/6; 435/472; 435/475; 435/476; 536/23.4

(58) Field of Classification Search .............. 435/6, 435/235.1, 320.1, 69.1, 69.7; 536/23.1
See application file for complete search history.

(56) References Cited

U.S. PATENT DOCUMENTS

| | | | |
|---|---|---|---|
| 5,223,409 A | 6/1993 | Ladner et al. ............ 435/69.7 |
| 5,403,484 A | 4/1995 | Ladner et al. ............ 435/235.1 |
| 5,498,538 A | 3/1996 | Kay et al. |
| 5,571,698 A | 11/1996 | Ladner et al. ............ 435/69.7 |
| 5,693,489 A | 12/1997 | Studier et al. |
| 5,766,905 A | 6/1998 | Studier et al. ............ 435/172.3 |
| 5,770,356 A * | 6/1998 | Light et al. .................... 435/5 |
| 5,837,242 A | 11/1998 | Holliger et al. |
| 5,885,793 A | 3/1999 | Griffiths et al. |
| 6,172,197 B1 | 1/2001 | McCafferty et al. |
| 2002/0197606 A1 | 12/2002 | Craig |
| 2002/0198162 A1 | 12/2002 | Punnonen et al. ............ 514/44 |
| 2003/0108885 A1 | 6/2003 | Schultz et al. .................. 435/6 |
| 2003/0186221 A1 | 10/2003 | Lockhart et al. ................ 435/5 |

FOREIGN PATENT DOCUMENTS

WO      WO 01/18234 A1      3/2001

OTHER PUBLICATIONS

Hoogenboom et al. "Multi-Subunit Proteins on the Surface of Filamentous Phage: Methodologies for Displaying Antibody (Fab) Heavy and Light Chains" Nucl. Acids. Res. 19(15):4133-4137 (1991).
Huang et al. "Use of the Arabinose $P_{bad}$ Promoter for Tightly Regulated Display of Proteins on Bacteriophage" Gene 251:187-197 (2000).
Lucic et al. "Secretion in *Escherichia coli* and Phage-Display of Recombinant Insulin-Like Growth Factor Binding Protein-2" J. Biotech 61:95-108 (1998).
Mikawa et al. "Surface Display of Proteins on Bacteriophage 2 Heads" J. Mol. Biol. 262:21-30 (1996).
Ward et al. "Retrieval of Human Antibodies from Phage-Display Libraries Using Enzymatic Cleavage" J. Imm. Meth. 189(1):73-82 (1996).
International Search Report, mailed on Dec. 19, 2003, for PCT patent application No. PCT/US03/24221, filed on Aug. 1, 2003, 5 pages.
Condron et al., An analysis of sequences stimulating frame shifting in the decoding of gene 10 of bacteriophage T7 Nucleic acid Res. 19 (20) 5607-12 (1991).
Condron et al., Frame shifting in gene 10 of bacteriophage T7 J. Bacteriol. 173 (21) 6998-7003 (1991).
Sipley et al., Bacteriophage T7 morphogenesis and gene 10 frame shifting in *Escherichia coli* showing different degrees of ribosomal fidelity Gen. Genet. 230 (3) 376-84 (1991).
Pope et al., In vitro selection of a high affinity antibody to oestradiol using a phage display human antibody library Immunotech. (1996) 209-217.
Rosenberg, A et al., T7 Select Phage display system: A powerful new protein display system based on bacteriophage T7 inNovations 6 (Dec. 1996).
Vaughan et al., Human antibodies with sub-nanomolar affinities isolated from a large non immunized phage display library Nat. Biotech. (1996) 14 309-314.
Hoogenboom, H. Designing and optimizing library selection strategies for generating high affinity antibodies. TIBTECH (Feb. 1997) 15 62-70.
Nilsson, J et al., Affinity fusion strategies for detection, purification, and immobilization of recombinant proteins. Prot. Exp. & Pur. (1997) 11 1-16.
Hoogenboom, H et al., Antibody phage display technology and its applications Immunotech. (1998) 4 1-20.
De Haard et al., A large non-immunized human Fab fragment phage library that permits .. J. Biol. Chem. (1999) 274 (26) 18218-28230.
Wycuff et al. Generation of AraC-araBAD promoter-regulated T7 expression system Analytical Biochemistry (2000) 277 67-73.
Lowman, H.B. "Bacteriophage Display and Discovery of Peptide Leads for Drug Development" (1997) vol. 26: 401-424.

* cited by examiner

*Primary Examiner*—Scott D. Priebe
*Assistant Examiner*—Michael Burkhart
(74) *Attorney, Agent, or Firm*—Wilson, Sonsini, Goodrich & Rosati

(57) ABSTRACT

The present invention provides an advance in phage display technology by permitting the uncoupling of the propagation of phages containing inserted sequences encoding heterologous polypeptides from the expression of said polypeptides. The invention provides phage constructs and methods for their use to permit phage coat protein expression, and thus phage propagation, in the absence of display of heterologous polypeptides, which may be expressed as a fusion with said coat protein in a regulated manner.

11 Claims, 4 Drawing Sheets

Improved Clone Collections in ATV Phage – Dramatically Reduced Mutation Rate

After one round of growth and expression:

| Gene | w.t./mutant | |
|---|---|---|
| | 10-3 | ATV |
| CamK IV | 0/6 | 6/0 |
| Glycerol Kinase | 0/4 | 6/0 |
| MAPK 9 | 6/0 | 6/0 |
| Mevalonate Kinase | 6/0 | 6/0 |
| TEK Receptor Tyrosine Kinase (1124 aa) | 2/2 | 4/0 |
| LIM Domain Kinase 2 (contains zinc finger domain) | 1/4 | 6/0 |

FIGURE 4

SEQUENCE LISTING

<160> NUMBER OF SEQ ID NOS: 1

<210> SEQ ID NO 1
<211> LENGTH: 17
<212> TYPE: DNA
<213> ORGANISM: T7 Virus

<400> SEQUENCE: 1
taatacgact cactata                                                17

UNCOUPLING OF DNA INSERT PROPAGATION AND EXPRESSION OF PROTEIN FOR PHAGE DISPLAY

TECHNICAL FIELD

The present invention relates to an improvement in phage display technology based on expression of a fusion nucleic acid construct containing nucleic acid sequences encoding a phage coat protein and a heterologous polypeptide. Expression of such a nucleic acid construct produces a fusion protein which is assembled into a phage particle that propagates the construct and displays the heterologous polypeptide on the particle surface. The present invention provides nucleic acid constructs and methods for their use which may be used to uncouple propagation of sequences encoding the phage coat protein and the heterologous polypeptide from expression and display of the heterologous polypeptide.

BACKGROUND ART

Phage display has been known and widely applied in the biological sciences and biotechnology (see U.S. Pat. Nos. 5,223,409; 5,403,484; 5,4571,698; 5,766,905; and the references cited therein). The methodology utilizes fusions of nucleic acid sequences encoding foreign polypeptides of interest to sequences encoding phage coat proteins to display the foreign polypeptides on the surface of bacteriophage particles. Applications of the technology include the use of affinity interactions to select particular clones from a library of polypeptides, the members of which are displayed on the surfaces of individual phage particles. Display of the polypeptides is due to expression of sequences encoding them from phage vectors into which the sequences have been inserted. Thus a library of polypeptide encoding sequences are transferred to individual display phage vectors to form a phage library that can be used to screen for polypeptides of interest.

Phage display has been used in a variety of ways and has also been modified to facilitate the isolation of the displayed polypeptide. Ward et al. (J. Imm. Meth. 189(1):73–82, 1996) describe the introduction of sequence encoding an enzymatic cleavage site between sequences encoding a human IgG1 polypeptide and a truncated M13 phage gene III. After expression on a phage surface, the polypeptide was separable from the phage by enzymatic cleavage.

Phage display based upon filamentous bacteriophage fd has also been modified to utilize sequences encoding a heterologous polypeptide and a sequence encoding a phage protein such that expression of the polypeptide may be in a soluble form or as a fusion with the phage coat protein depending upon the cell line used (see Hoogenboom et al., Nucl. Acids Res. 19(15):4133–7, 1991, and Lucic et al., J. Biotech. 61:95–108, 1998). Similarly modified sequences have been used in bacteriophage λ based display systems to conditionally express heterologous polypeptides on bacteriophage λ heads (see Mikawa et al., J. Mol. Biol. 262: 21–30, 1996).

A constraint associated with phage display, however, is where expression of a heterologous polypeptide affects the viability of the host cell used to propagate the phage library or used to produce phage for display. One approach to address this constraint has been by the use of a tightly regulated promoter to control the expression of fusions of a heterologous polypeptide and a phage coat protein, and thus control display of proteins on phage (see Huang et al. Gene, 251:187–197, 2000). This approach does not fully address a second difficulty, however, where the presence a heterologous polypeptide as a fusion with a phage coat protein results in interference with the phage life cycle. A possible approach to address both interference with phage life cycle and negative effects on host cell viability is to use modified regulators of transcription and/or translation that decrease the level of expression of the heterologous polypeptide.

Citation of documents herein is not intended as an admission that any is pertinent prior art. All statements as to the date or representation as to the contents of these documents is based on the information available to the applicant and does not constitute any admission as to the correctness of the dates or contents of these documents.

DISCLOSURE OF THE INVENTION

The present invention provides the ability to uncouple the propagation and expression of the phage surface protein and the heterologous polypeptide that are coupled during the practice of phage display. The uncoupling is controllable, and provides the advantage of being able to propagate a phage display fusion construct without expression of the heterologous polypeptide. In preferred embodiments, propagation of a phage display fusion construct is uncoupled from expression of the encoded heterologous polypeptide.

The invention generally provides for the propagation of a phage display construct under two conditions relative to expression of the phage surface protein and the heterologous polypeptide. The first condition is nucleic acid propagation, by packaging the construct in a phage particle, in the presence of expressed phage surface protein and the absence of expressed heterologous polypeptide. The second condition is nucleic acid propagation in the presence of expressed phage surface protein and expressed heterologous polypeptide as a fusion protein. The latter of these two conditions is where the packaged phage may be used for phage display. Preferred constructs for the practice of the invention under these conditions are phage genome based constructs that require phage production for propagation of phage encoded nucleic acid sequences.

The ability to uncouple propagation from expression of the heterologous polypeptide is an aspect of the invention that is ideally suited for situations where expression of the heterologous polypeptide may be toxic to the host cell or detrimental to the normal phage life cycle. In another aspect, the invention also permits the controlled uncoupling of expression of the phage surface protein from expression of the heterologous polypeptide. This is of particular advantage in situations where expression of the heterologous polypeptide negatively affects the growth or viability of the host cell or the production of viable phage particles. An additional beneficial effect is that a collection of sequences encoding heterologous polypeptides in phages of the invention may be propagated or maintained without loss of complexity (or representation of individual sequences) due to detrimental effects from expression of some sequences.

The present invention also advantageously permits the use of unmodified regulatory sequences controlling transcription and/or translation to permit high level expression of the phage surface protein, optionally as a fusion with the heterologous polypeptide for phage display. Stated differently, the ability to uncouple expression of the phage surface protein from the heterologous polypeptide permits the use of unattenuated promoters and translational signals (e.g. sites of ribosome binding and/or entry) without significant negative effects on phage propagation or host cell viability.

Alternatively, the invention may be practiced with regulatory sequences modified to result in increased expression because the ability to uncouple expression of the phage surface protein from expression of the heterologous polypeptide prevents, or decreases the effect of, the latter from affecting either phage propagation or host cell viability.

The present invention provides phage derived nucleic acid constructs and methods of using them to uncouple propagation of a nucleic acid construct from expression of a heterologous polypeptide encoded by sequences present in the construct. A phage derived nucleic acid construct of the invention generally comprises a nucleic acid molecule encoding both a phage surface protein and a heterologous polypeptide such that they are capable of being expressed as a fusion protein. As such, they are operably linked by being in the same reading frame and by being under the control of the same promoter and/or regulatory region. The operable linkage between the sequences encoding a phage surface protein and a heterologous polypeptide includes a termination (or "stop") codon inserted between the two sequences such that expression of the fusion protein requires suppression of premature termination of translation at the termination codon. Optionally, the linkage also includes a sequence encoding an enzymatic cleavage site such that after expression as a fusion protein with the phage surface protein, the heterologous polypeptide may be released from phage particles by enzymatic cleavage. A non-limiting example of such a cleavage site is that recognized and cleaved by the tobacco etch virus (TEV) protease.

The arrangement of the coding sequences for a phage surface protein and a heterologous polypeptide preferably occurs, in a 5' to 3' orientation, the phage surface protein encoding sequence followed by the heterologous polypeptide encoding sequence. Of course the invention provides for the optional presence of sequences between those encoding the phage surface protein and the heterologous polypeptide. Non-limiting examples of such optional sequences include linkers and/or sequences encoding a cleavage site recognized by a protease. The coding sequences may be under the control of a native or heterologous promoter present in the phage derived nucleic acid construct. In preferred embodiments of the invention, the construct is derived from a phage genome and the promoter is endogenous to that genome. A non-limiting example is the use of a T7 phage based construct and the use of a T7 promoter. Alternatively, the promoter may optionally be inducible to provide further control of gene expression, such as, but not limited to, the lac UV5 promoter which is induced by IPTG.

The invention is preferably practiced by use of phage genomes that are conservatively modified to contain heterologous polypeptide encoding sequences fused to a phage surface protein as described herein. The modifications are preferably limited to those that are necessary for the introduction of the necessary sequences encoding the heterologous polypeptide, the termination codon, optional cleavage sequences, and any sequences to facilitate the cloning or linking of various sequences. The modified phage genomes preferably retain the regulatory and coding sequences found therein. Preferred phage genomes for the practice of the invention are those of lytic phages, not limited to T7, T4, T3 and lambda phage, and filamentous phages.

The sequences encoding heterologous polypeptides are preferably those of a cDNA or genomic library as known in the art or prepared by art known methods. The sequences may also be simply open reading frames (ORFs) or DNAs complementary to cellular transcripts as known or identified by the skilled person in the art. The cDNA, genomic, or ORF sequences may be from any source, including cell lines and organisms, and are introduced into the phage derived nucleic acid constructs such that they may be conditionally expressed in accord with the present invention and as fusion proteins with a phage surface protein. Preferably, the library sequences contain cDNAs prepared from a cell type (cell specific cDNAs) of interest, such as, but not limited to, eukaryotic or prokaryotic cells, normal or diseased cells or tissues, human cells, non-human primates, mammals, fungi, plants, bacteria or other naturally occurring sources. Alternatively, the library sequences may encode a particular type of functionality, such as, but not limited to, an enzymatic activity, a receptor, a nucleic acid binding protein, or a component of a signaling pathway. In a further embodiment, the sequences may be artificially modified forms of naturally occurring sequences. The sequences may also be from a source that is selected or non-selected, such as, but not limited to, cells or tissues that have been treated with a drug or other chemical agent or cells that have not been so treated.

The invention also provides a suppressor construct capable of conditionally expressing a suppressor tRNA molecule under the control of a regulated promoter, such as, but not limited to, an inducible promoter. Preferably, the promoter is the arabinose $P_{BAD}$ promoter along with its regulatory gene araC or other inducible promoter known in the art. Alternative regulatory systems for use as a regulated promoter include, but are not limited to, the tet operon system, the lac operon system, and the lpp-lac operon system. Preferably, a suppressor construct is introduced into a cell under selective pressure (such as by selection for a marker expressed by the suppressor construct), or such that it is stably integrated, to form a suppressor cell line.

Particularly preferred for the practice of the invention is the use of a "tunable" promoter that can control the expression of a suppressor tRNA in an incremental fashion. This permits the suppression of the termination codon in a regulated manner such that the amount of heterologous polypeptide expressed, and incorporated into the phage surface, is "tunable" by controlling the expression of the suppressor. Such control of heterologous polypeptide expression on the phage surface may be viewed as controlling the "valency" of the heterologous polypeptide on the phage surface. Preferred constructs of the invention are phage derived and capable of producing phage with "tunable valency". Such phage may be termed "tunable valency" (or "TV") phage.

The combination of a phage derived nucleic acid construct and a suppressor construct is referred to herein as an expression system of the invention such that the suppression of the termination codon in the phage derived construct is dependent upon expression of the suppressor tRNA encoded by the suppressor construct. Stated differently, an expression system of the invention permits the uncoupling of expression of the phage surface protein and a heterologous polypeptide such that the phage protein may be expressed without co-expression of the heterologous polypeptide as a fusion product with the phage protein.

The invention also provides cells containing an expression system of the invention such that expression of the heterologous polypeptide is at least conditional upon expression of the suppressor tRNA. In the absence of suppression of the termination codon, the phage surface protein will be expressed without expression of the heterologous polypeptide. Expression of the suppressor tRNA molecule permits expression of a fusion protein comprising both the phage surface protein and a heterologous polypeptide. In embodiments of the invention where the construct, capable of expressing a fusion protein comprising both the phage surface protein and a heterologous polypeptide, is regulated by an inducible promoter, expression of the fusion protein would be conditional upon activation of the promoter and expression of the suppressor tRNA. This provides a means to conditionally express the heterologous polypeptide in the presence of suppressor tRNA expression.

Cells containing an expression system of the invention may be used to propagate the phage derived construct, by production of phage, in the absence of expression of a heterologous polypeptide. This is readily practiced by not inducing expression of the suppressor tRNA. Alternatively, the phage display construct may be propagated in a cell that does not contain a suppressor construct such that suppression is not possible. These phage particles produced will have a minimal opportunity to express the heterologous polypeptide due to spurious "readthrough" suppression of the termination codon. Optionally, the propagation of the phage display construct in such cells may be augmented by the expression of the phage surface protein by another sequence, optionally regulated, in the cell. The expression of phage surface protein may be at set at high levels to further suppress the presence of heterologous polypeptide on phage surfaces due to dilution of any fusion proteins resulting from a spurious "readthrough" event from being incorporated into the phage surface.

When display of heterologous polypeptide is desired, the product phage may be introduced into cells with a suppressor construct to express phage displaying the heterologous polypeptide on the phage surface.

Propagation without expression of the heterologous polypeptide or a minimum level of heterologous polypeptide expression has the additional advantage of reducing emergence (selection) of mutations in sequences encoding a heterologous polypeptide. Stated differently, use of the present invention results in a lower mutation frequency of sequences encoding heterologous polypeptides. This follows because the polypeptides are not expressed and thus cannot affect the survival characteristics of either the phage or the host cell. This is of particular advantage in cycles of propagation and amplification of phage that occur between selection rounds, especially where the selected phage have low multiplicity of infection (m.o.i) frequencies. Stated differently, phage that are selected in a given round may be used to infect cells (even at low m.o.i.) followed by propagation/amplification in the absence of heterologous polypeptide expression. Such propagation/amplification results in the production of phage at a high m.o.i. and the absence of selective pressure caused by expression of the heterologous polypeptide. The resultant phage can be used to infect cells in combination with induction of heterologous polypeptide expression (by inducing expression of the suppressor tRNA) to produce larger amounts of phage particles displaying the heterologous polypeptide on their surfaces for use in the next round of selection.

The ability to propagate/amplify phage containing sequences encoding heterologous polypeptides without expression of the polypeptides may be advantageously used for the maintenance of phage library stocks and collections of nucleic acid clones. It also advantageously permits phage propagation in the absence of a growth bias (distinct from selective pressure) either against phage that would grow slowly due to expression of a heterologous polypeptide or for phage that would grow faster due to expression of a heterologous polypeptide. The invention thus permits the propagation of phage libraries and collections without loss of complexity due to loss of, or overrepresentation of, individual clones.

The absence of a growth bias also permits use of the present invention to assist in plaque selection with reduced bias and increased counting efficiency because of reduced differences in growth and lysis rates in the absence of heterologous polypeptide expression.

The present invention can be used or adapted for use in phage display of polypeptides for selection or screening as known and used in the art. For example, the present invention may be used to display polypeptides from a cDNA library of a particular cell type as a population (or library) of phage particles, each of which displays a polypeptide encoded by one clone (or member) of the cDNA library. The phage particles may then be selected based on affinity interactions with a molecule of interest, such as, but not limited to, another polypeptide or a small organic compound. Selected phage particles may be isolated, propagated/amplified (optionally in the absence of expression of the heterologous polypeptide), and used to display the encoded polypeptides for additional round(s) of selection. Following selection, the sequences encoding the selected polypeptide may be isolated and/or sequenced to identify the polypeptide. The phage constructs containing them may also be used as the source of the encoding sequence for subsequent use in preparation of the polypeptide

BRIEF DESCRIPTION OF THE DRAWINGS

FIG. 4 shows a reduction in the observed mutation rate with use of an ATV phage display construct of the invention as described in the Examples.

MODES OF CARRYING OUT THE INVENTION

Figure 1:
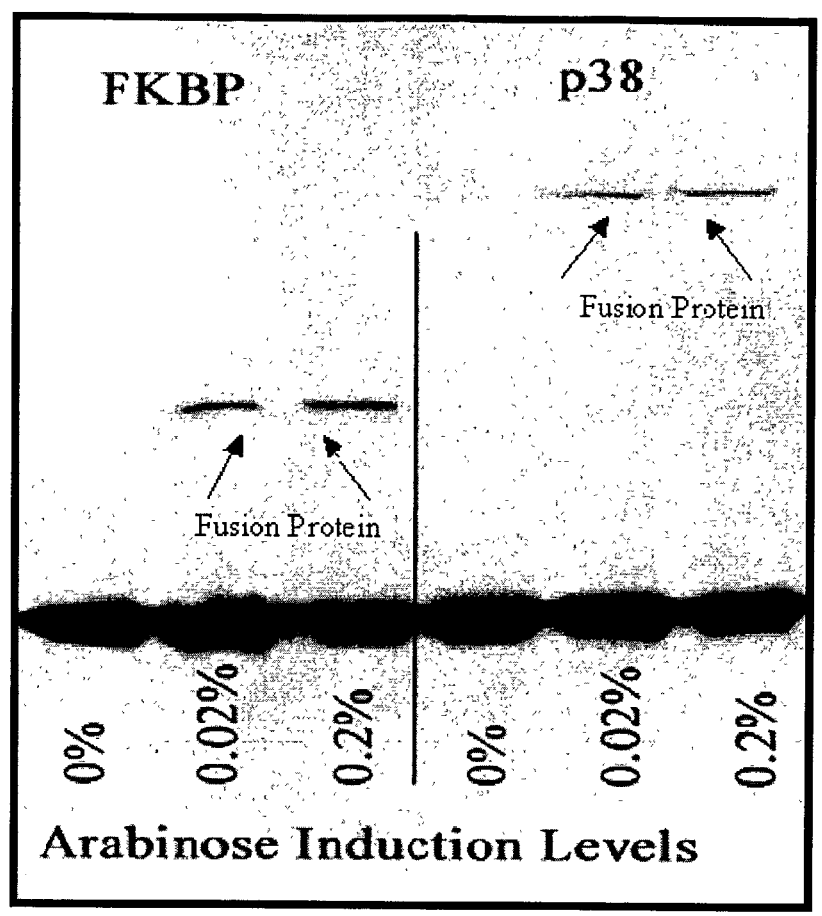
FIG. 1 shows that display of a polypeptide on phage surfaces can be controlled by growing phage in either the presence or absence of arabinose to control expression of a suppressor tRNA.

A phage derived nucleic acid construct of the invention comprises a nucleic acid molecule containing a promoter and/or regulatory region operably linked to a coding sequence for a phage surface protein linked in frame to a sequence containing a termination codon and in frame to a sequence encoding a heterologous polypeptide. As used herein, "phage derived" refers to a construct comprising one or more nucleic acid sequences found in naturally occurring polynucleotides encoding phage gene products. The term "operably linked" refers to a functional linkage between nucleic acid sequences such that the linked promoter and/or regulatory region functionally controls expression of the coding sequence. It also refers to the linkage between coding sequences such that they may be controlled by the same lined promoter and/or regulatory region. Such linkage between coding sequences may also be referred to as being linked in frame or in the same coding frame such that a fusion protein comprising the amino acids encoded by the coding sequences may be expressed.

The term "phage surface protein" refers to any protein normally found at the surface of a bacteriophage that can be adapted to be expressed as a fusion protein with a heterologous polypeptide and still be assembled into a phage particle such that the polypeptide is displayed on the surface of the phage. Preferably, the phage surface protein, and thus the phage derived nucleic acid construct, is that of a lytic phage such as, but not limited to λ, T4 and T7. Particularly preferred embodiments of the invention utilize a T7 phage coat protein, such as, but not limited to, the product of gene 10, and a T7 derived construct. Other non-limiting examples of phage surface proteins include the gene III capsid protein of filamentous bacteriophage, the gene VIII capsid protein of filamentous phage, and the capsid D protein (gpD) of bacteriophage λ. As appreciated by the skilled artisan, the choice of a phage surface protein is to be made in combination with a consideration of the phage derived construct and the cell to be used for propagation thereof.

The term "heterologous polypeptide" refers to a polypeptide that is not normally found as encoded by the phage from which sequences have been used to prepare a phage derived construct of the invention. Preferred heterologous polypeptides are those encoded by nucleic acid molecules or open reading frames (ORFs) found in eukaryotic or prokaryotic cells, especially those from human beings, plants, plant cells, and research organisms and animals. Non-limiting examples include bacteria, mice, rats, fruit flies, yeast, rabbits, non-human primates and zebrafish. Other preferred nucleic acid molecules are from other mammals, particularly those important to agricultural applications (such as, but not limited to, cattle, sheep, horses, and other "farm animals") and for human companionship (such as, but not limited to, dogs and cats). Another source of nucleic acid molecules are those of pests, such as insects, weeds, fungi, viruses and unicellular organisms. In a particularly preferred embodiment, the nucleic acid molecules or ORFs are those encoding, or suspected of encoding, clinically relevant gene products including potential targets for the identification of drugs for particular disease indications.

Termination codons are known in the art, with UAG being referred to as the amber codon and UAA being referred to as the ochre codon. UGA may also be used when appropriate. The choice of termination codon can also be augmented by introduction of particular sequences around the codon. For example, amber codons followed by a purine base (adenine or guanine) have been reported as well suppressed under certain conditions.

A variety of different phage derived constructs may be used in the practice of the invention. In preferred embodiments of the invention, the constructs are phage genomes that have been modified to be capable of conditionally expressing a heterologous polypeptide, as a fusion protein with a phage surface protein, as discussed herein. In other embodiments of the invention, the ability to express a fusion protein is regulated in part by use of a regulated promoter or other regulatory region (e.g. an inducible promoter such that in the absence of induction, expression controlled by them is low or undetectable). Non-limiting examples of inducible promoters include the lac promoter, the lac UV5 promoter, the arabinose promoter, and the tet promoter.

Constructs of the invention derived from a phage genome preferably contain sequences encoding the phage gene products necessary to package an infective phage comprising a fusion of a phage surface protein and a heterologous polypeptide. The conditional expression of heterologous polypeptide would thus be conditional upon expression of the necessary suppressor tRNA. In embodiments where a construct of the invention does not encode the phage gene products necessary for phage propagation, the missing products may be provided by expression of sequences present in the cell used to propagate the phage. In other embodiments of the invention, a phage derived construct would contains sequences from a non-phage vector to assist in the propagation and manipulation of the nucleic acid molecule. Selection of appropriate vectors, including phage based vectors, for propagation or transfer of nucleic acids is well known in the art. The requisite techniques for vector construction, introduction of the vector into the host, and propagation or expression in the host are routine to those skilled in the art. Non-limiting examples of vectors that can be used in the present invention are described below.

The arrangement of the coding sequences for a phage surface protein and a heterologous polypeptide preferably occurs, in a 5' to 3' orientation, the phage surface protein encoding sequence followed by a sequence containing a (suppressible) termination codon and a heterologous polypeptide encoding sequence. The term "5'" (five prime) generally refers to a region or position in a polynucleotide 5' (upstream) from another region or position in the same polynucleotide. The term "3'" (three prime) generally refers to a region or position in a polynucleotide 3' (downstream) from another region or position in the same polynucleotide. The sequence containing a termination codon may also be referred to as a linker that contains sequences encoding other amino acids in frame with both the phage surface protein encoding sequence and the heterologous polypeptide encoding sequence. The linker may optionally contain a sequence encoding an enzymatic cleavage site. Non-limiting examples of such sites include subtilisin, H64A subtilisin, Genenase I, TEV protease, thrombin, factor Xa, and enterokinase.

Sequences encoding heterologous polypeptides are readily prepared by preparation of cDNA or isolation of genomic nucleic acid sequences from cells as selected by the skilled person. The sequences may also be simply open reading frames (ORFs) as known or identified in the art, whether or not a function has been determined for the polypeptide encoded by the sequence. The sequences may also be those encoding cellular factors having a particular functionality, such as an enzymatic activity or receptor function. Constructs containing these sequences are advantageously used in embodiments of the invention where phage displaying the polypeptides encoding them are contacted with compounds known, or thought, to target a particular type of cellular functionality. For example, and without limiting the invention, sequences encoding kinase activities may be used to display them for selection with a compound known, or thought, to bind kinases in competition under various conditions. This provides the ability to identify the actual kinase(s) that bind the compound under different conditions to determine the specificity of the interactions.

The invention also provides a suppressor construct capable of conditionally expressing a suppressor tRNA molecule under the control of a regulated promoter. Suppressor constructs may be derived from various vectors, including those discussed below, and are preferably able to be maintained in a cell at high copy number to enhance the suppression effect. The phage derived and suppressor constructs of the invention are preferably selectable based upon different markers present on each construct. Non-limiting examples of such markers include resistance to ampicillin, kanamycin, tetracycline, carbenicillin, chloramphenicol, and streptomycin. Selection is readily performed by contacting the cells with the appropriate selection agent for the marker used. Of course the amount of the selection agent must be sufficient to result in cell death, and such amounts are either known or readily determined by the skilled person without undue experimentation.

The suppressor tRNA is of course selected to be capable of suppressing the termination codon used in the phage derived construct of the invention. Thus an amber suppressor tRNA would be used where UAG is the termination codon while an ochre suppressor tRNA would be used where UAA is the termination codon. The suppressor tRNA may direct the insertion of any amino acid (especially one of the twenty naturally occurring amino acids used in translation), but preferably, it directs insertion of alanine or glutamic acid.

The constructs of the invention are introduced into cells by any means known in the art without undue experimentation. Of course infection of susceptible cells by phage may be used. Methods developed subsequent to the instant disclosure may also be used. Preferred cells of the invention are wild type, and thus not able to suppress the termination codon present between the sequences encoding the phage surface protein and the heterologous polypeptide.

Cells for the practice of the invention may be selected by the skilled person in light of the instant disclosure without undue experimentation. Non-limiting examples include E. coli cells and other bacterial cells appropriate for phage propagation and/or phage infection. Preferred cells are those that do not suppress the termination codon(s) used in the practice of the invention. Such cells are particularly useful in the phage production, without expression of the heterologous polypeptide and optionally with the expression of excess phage surface protein. A non-limiting example of such cells is the E. coli BL21 cell. When used in phage production without display of the heterologous polypeptide, the cells may contain a construct capable of expressing the sequence encoding the phage surface protein (and fused to the sequence encoding the heterologous polypeptide) under a regulated promoter. A non-limiting example of such cells is the E. coli BLT5615 cell available from Novagen, which is a derivative of BL21 cells. BLT5615 cells are capable of expressing the T7 phage coat protein under the control of an IPTG inducible promoter.

Of course cells that endogenously express an appropriate suppressor tRNA may also be used to package a phage derived construct with expression of the fusion protein on phage particle surfaces. Such cells are particularly useful in the production of phage that display the heterologous polypeptide on its surface, although their use would not permit the control of such expression by regulating expression of the suppressor tRNA. Such controllable expression of suppressor tRNA is provided by the suppressor constructs of the invention.

As evident from the discussion herein, the combination of a phage derived nucleic acid construct and a suppressor construct couples expression of a suppressor tRNA to expression of a heterologous protein. Because expression of the suppressor tRNA is conditional, the expression of the heterologous protein is conditional. Thus without induction of expression of the suppressor tRNA, a phage derived construct would simply be propagated via expression of the phage surface protein to permit packaging of phage particles without display of the heterologous polypeptide on their surfaces. If expression of the tRNA is induced, then display of the heterologous polypeptide on the surface of phage particles occurs.

The invention may also be practiced with cells modified to assist in the propagation of phage derived constructs and the packaging of phage particles. One example of such cells are those that contain an additional construct (or second genetic element, optionally integrated into the cellular genome) for expression of the phage surface protein. These cells would be capable of expressing additional phage surface protein, optionally under regulatory control such as by use of an inducible promoter, to ensure that sufficient phage surface protein is produced for effective packaging of a phage derived construct. As noted above, the use of such constructs to express additional phage surface protein can also be used to dilute out the incorporation of fusions of surface protein and heterologous polypeptide that may occur due to spurious expression events in the cell.

The present invention can be used or adapted for use in phage display of polypeptides for selection or screening with a test compound. For example, the present invention may be practiced by introducing the constructs disclosed herein into a cell to produce a library of phage particles to determine which displays a polypeptide on its surface that interacts with a test compound. Preferably, the interaction includes binding specific interactions between the polypeptide and the test compound. Detection of the interaction permits the polypeptide to be identified as interacting with the compound. Detection of the interactions may also be used to select phage particles for isolation, subsequent propagation and/or amplification, and/or further rounds of selection. Preferably, one, two, three, four, or five additional rounds of selection are used to identify phage that interact with a test compound.

The sequences encoding the heterologous polypeptides in the selected phage may be isolated and identified from by a variety of methods well known in the art. Non-limiting examples include simple PCR, mediated by primers complementary (in whole or in part) to known (phage construct) sequences flanking the coding region in the genetic material of the selected phage, and direct isolation of phage genetic material, such as via excision by the use of appropriate restriction enzymes (optionally followed by cloning into another vector or nucleic acid molecule, also known as "subcloning"). The coding sequences may also be sequenced by methods known in the art.

Vectors

As used herein, the term "vector" refers to a nucleic acid molecule capable of transporting another nucleic acid to which it has been linked. The term includes phage based vectors such as, but not limited to phage based plasmids and "phagemids". One type of vector is an episome, i.e., a nucleic acid molecule capable of extra-chromosomal replication. Vectors may also be used to deliver nucleic acid molecules into a cell for integration into the cellular genome. Preferred vectors for practice of the invention are those derived from phage genomes that are capable of expressing the gene products necessary for packaging of phage particles containing the vector.

Vectors used in recombinant DNA techniques are often in the form of "plasmids" which refer to circular double stranded DNA loops which are maintained episomally. In addition, the invention is intended to include other forms of vectors which serve equivalent functions and which become known in the art subsequently hereto.

Vectors can be used for the expression of polynucleotides and polypeptides. Generally, such vectors comprise cis-acting control regions effective for expression in a host operably linked to the polynucleotide to be expressed.

Appropriate trans-acting factors either are supplied by the host, supplied by a complementing vector, or supplied by the vector itself upon introduction into the host.

In certain circumstances, the vectors provide for specific expression. Such specific expression may be inducible expression, expression only in certain types of cells, or both inducible and cell-specific. Vectors can be induced for expression by environmental factors that are easy to manipulate, such as temperature and nutrient additives. A variety of vectors such as constitutive and inducible expression vectors for use in prokaryotic and eukaryotic hosts, are well known and employed routinely by those of skill in the art.

A great variety of vectors can be used in the invention. Such vectors include, but are not limited to, vectors derived from bacterial plasmids, from bacteriophage, from yeast episomes, from yeast chromosomal elements, from mammalian viruses, from mammalian chromosomes, and vectors derived from combinations thereof, such as those derived from plasmid and bacteriophage genetic elements, such as cosmids and phagemids. Generally, any vector suitable to maintain, propagate or express polynucleotides in a cell may be used.

The following vectors, which are commercially available, are provided by way of non-limiting example as an alternative to vectors that are derived from phage genomes. Among vectors for use in bacteria pQE70, pQE60, and pQE-9, available from Qiagen; Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. These vectors are listed solely by way of illustration of the many commercially available and well known vectors that are available to those of skill in the art for use in accordance with the present invention. It will be appreciated that any other plasmid or vector suitable for, for example, introduction, maintenance, propagation, and/or expression of a polynucleotide or polypeptide of the invention in a host may be used in this aspect of the invention.

The appropriate DNA sequence may be inserted into the vector by any of a variety of well-known and routine techniques. In general, a DNA sequence for expression is joined to a vector by cleaving the DNA sequence and the vector with one or more restriction endonucleases and then joining the restriction fragments together using a DNA ligase activity, such as T4 DNA ligase. Procedures for restriction and ligation that can be used are well known and routine to those of skill in the art. Suitable procedures in this regard, and for constructing vectors using alternative techniques, which also are well known and routine to those skilled in the art, are set forth in great detail in Sambrook et al. cited elsewhere herein.

It should be understood that the choice and/or design of the vector may depend on such factors as the choice of the host cell to be transformed and/or the type of protein(s) desired to be expressed. Moreover, the vector's copy number, the ability to control that copy number, and the expression of any other proteins encoded by the vector, such as antibiotic markers, should also be considered.

Unless defined otherwise all technical and scientific terms used herein have the same meaning as commonly understood to one of ordinary skill in the art to which this invention belongs.

Having now generally described the invention, the same will be more readily understood through reference to the following examples which are provided by way of illustration, and are not intended to be limiting of the present invention, unless specified.

EXAMPLE 1

Phage Constructs and Cell Lines

Using T7 as a representative example, a phage display construct derived from the T7 genome has been constructed in accord with the present invention. The complete sequence of the T7 genome is known in the art. The construct has the coat protein encoded by gene 10 under the control of a wildtype T7 promoter (comprising TAATACGACTCACTATA (SEQ ID NO: 1)) and Shine-Delgarno ribosome entry site (comprising GAAGGAGA). Both these sequences are upstream (5') of the ATG start codon of gene 10, which has been modified at its 3' end to contain restriction sites to readily permit fusion with a sequence encoding a heterologous polypeptide as described above and herein. This construct has been termed the "ATV" phage or ATV phage construct.

In alternative embodiments of the invention the T7 promoter may be deleted and/or the Shine-Delgarno sequences may be mutated to reduce the level of expression from gene 10 (whether alone or as a fusion with a sequence encoding a heterologous polypeptide). The Shine-Delgarno sequence may optionally be deleted to further decrease expression. With the use of such changes affecting expression of the coat protein, expression of the coat protein from another construct within the cell is preferred to provide sufficient coat protein for phage production. Preferably, such additional constructs are under the control of a regulatable promoter as described above and herein.

For constructing a suppressor construct, termed pBAD-tRNA$^{Ala/TAG}$, an amber tRNA suppressor under the control of the arabinose-inducible BAD promoter has also been introduced into a plasmid vector in accord with the present invention. This plasmid carries an origin of replication and a selectable chloramphenicol resistance marker. The plasmid also carries the araC regulatory gene that encodes a regulatory DNA binding protein that acts as a positive or negative regulator of the BAD promoter. In the presence of L-arabinose, transcription from the BAD promoter is induced, while in the absence of arabinose, transcription occurs at very low or undetectable levels. This low level can be further reduced in the presence of glucose, which acts as a negative regulator of the BAD promoter (see Guzman et al. J. Bact. 177(14):4121–4130, 1995).

The above described promoter system for the suppressor construct is also useful to permit different levels of activation with different concentrations of L-arabinose. It has been observed that the use of this construct resulted in a linear response in the range of 0.2% to 0.002%, final concentration, of L-arabinose (see FIG. 3). This construct is ideal for use in combination with the phage display construct of the invention in host cells such as BL21 or BLT5615 (Novagen Inc., Madison, Wis.), which are not adapted to grow in the presence of a suppressor tRNA but are ideal for the production of T7 phage for display. BLT5615 is especially preferred because it contains deletions of two important protease genes and two restriction-methylation defense systems as well as a vector expressing wildtype coat protein under an IPTG regulated promoter. Other strains for use in the practice of the invention include BLT5403 or any E. coli strain which does not suppress the termination codon used between sequences encoding the phage surface protein and the heterologous polypeptide in the phage construct.

As an example of the practice of the invention, the ATV (containing a sequence encoding a heterologous polypeptide fused to the gene 10 sequence) is introduced into host cells, optionally containing a construct for the expression of the gene 10 coat protein under control of an IPTG regulated promoter, for propagation of the ATV phage. The product phage may then be used to infect BLT5615 containing pBAD-tRNA$^{Ala/TAG}$ as described above such that induction with arabinose results in production of phage displaying the heterologous polypeptide on T7 phage particles. This may be practiced with a library of ATV phages containing various sequences encoding heterologous polypeptides.

EXAMPLE 2

Induction of Phase Display by Amber Suppression

Two different cDNA sequences were inserted into the ATV phage constructs containing the amber codon. The cDNAs encode the FK506 binding protein (FKBP) and the p38 mitogen activated protein (MAP) kinase (MAPK). BL21 cells containing pBAD-tRNA$^{Ala/TAG}$ were grown to log phase and induced for 30 minutes with two different concentrations of L-arabinose to cause expression of the suppressor tRNA$^{Ala/TAG}$. After induction, the cells were infected with ATV phage that contain cDNA inserts that encode either FKBP or p38 MAPK as a fusion with the gene 10 coat protein. The results of a Western blot of the resultant phage proteins are shown in FIG. 1, which clearly indicates that there is little or no detectable expression of the fusion protein in the absence of L-arabinose. The addition of L-arabinose at the two concentrations used increases expression of the fusion protein in an arabinose concentration dependent manner.

Figure 2:
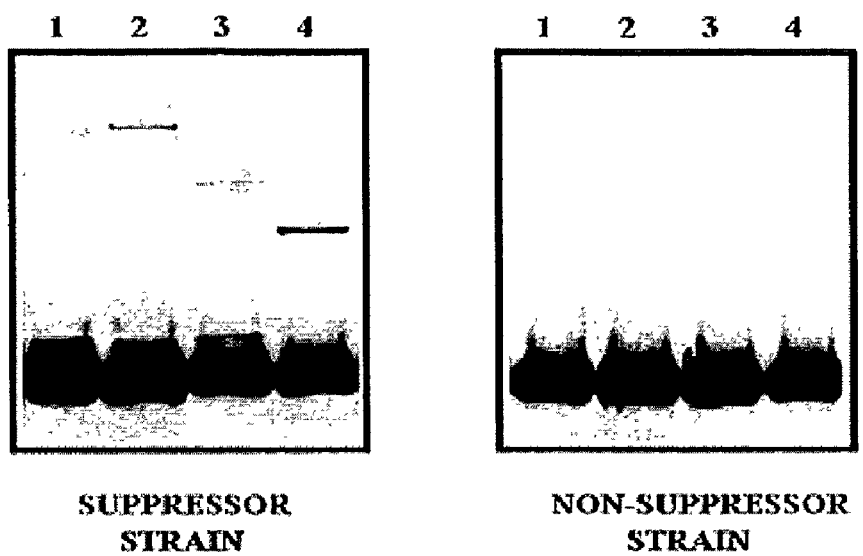
FIG. 2, panels A and B, show the expression of various cDNAs via phage derived nucleic acid constructs of the invention that have been introduced into a suppressor strain (panel A) and non-suppressor strain (panel B) of E. coli.

Similar results are seen with the introduction of cDNA inserts encoding glycogen synthase kinase 3 (83 kD), MAPK 10 (85 kD), adenylate kinase (66 kD) and cyclin-dependent kinase inhibitor 1A (55 kD), as shown in lanes 1–4, respectively, of FIG. 2, into phage constructs propagated in a suppressor strain (panel A) and non-suppressor strain (panel B). As shown, growth of the phage in a suppressor strain resulted in the expression of the cDNA inserts while growth in a non-suppressor strain resulted in no expression.

EXAMPLE 3

Dependence of Suppressor Activity on Arabinose Concentration

Figure 3:
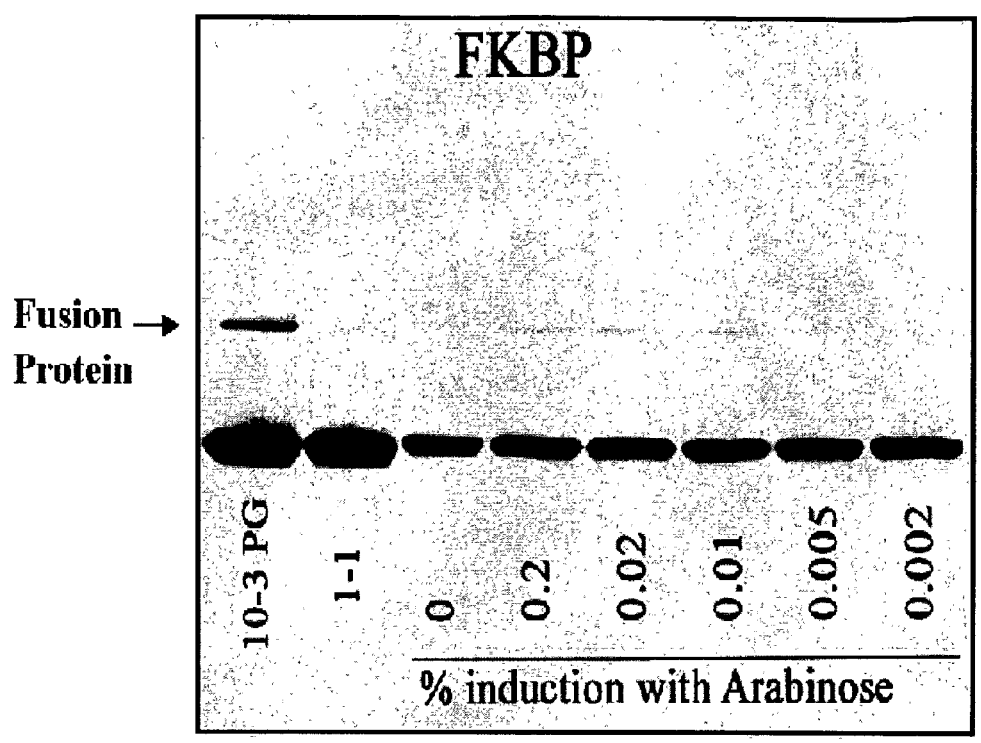
FIG. 3 shows the dependency of fusion protein expression on the level of suppressor tRNA expression via induction by various concentrations of L-arabinose.

The ATV-FKBP phage was used to infect BL21 cells grown to log phase and induced for 30 minutes with five different concentrations of L-arabinose (from 0.2% to 0.002%, final concentrations). In the same experiment, the level of fusion protein expression was compared to Novagen's T7 10-3 strain (high expressor) and T7 1-1 (low expressor) phage strains containing the same FKBP cDNA. The results of a Western blot analysis of the phage proteins are shown in FIG. 3, which shows that the amount of fusion protein produced is increased by increasing amounts of L-arabinose used for induction. The observed level of fusion protein produced in the ATV strain is higher than that observed for T7 1-1 but lower than that for T7 10-3 phage. Further increases in the expression with the ATV strain can be seen by reducing the amount of glucose in the medium of the cells. Lower glucose levels allow greater induction of the BAD promoter.

EXAMPLE 4

Improved Clone Collections in ATV Phase

The ability of the ATV phage to reduce the mutation rate of the sequence encoding a heterologous polypeptide is shown in FIG. 4. cDNAs encoding six proteins were introduced into Novagen's 10-3 T7 strain or the ATV phage followed by one round of growth (propagation) and expression. The number of wildtype cDNA sequences relative to mutated cDNA sequences are shown with use of the 10-3 or ATV strains. For all six cDNAs, use of the ATV strain resulted in no observed mutated sequences while mutant sequences were observed for four of the six cDNAs in the 10-3 strains. In particular, every cDNA encoding CamK IV and glycerol kinase was observed as mutated when the 10-3 phage was used.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

The invention claimed is:

1. An expression system comprising
   a modified T7 phage genome comprising a first nucleic acid molecule comprising a promoter and/or regulatory region operably linked, in a 5' to 3' orientation, to a sequence encoding a T7 phage coat protein operably linked in a 5' to 3' orientation to a sequence comprising a termination codon operably linked in a 5' to 3' orientation to a sequence encoding a heterologous polypeptide and
   a suppressor construct comprising an inducible promoter and/or regulatory region operably linked to a sequence encoding a suppressor tRNA corresponding to said termination codon.

2. The system of claim 1 wherein said promoter and/or regulatory region is endogenous to a T7 phage genome.

3. The system of claim 1 wherein said promoter and/or regulatory region is an endogenous T7 promoter.

4. The system of claim 1 wherein said inducible promoter and/or regulatory region is the arabinose BAD promoter and the araC regulatory gene.

5. The system of claim 1 wherein said sequence comprising said termination codon further comprises a linker sequence encoding an enzymatic cleavage site.

6. The system of claim 1 wherein said suppressor construct further comprises an expressible sequence encoding chloramphenicol resistance.

7. The system of claim 1 wherein said termination codon is selected from UAA and UGA.

8. The system of claim 1 wherein said termination codon is UAG.

9. The system of claim 1 wherein said suppressor tRNA is $tRNA^{Ala}$ or $tRNA^{Glu}$.

10. The system of claim 1 wherein said suppressor tRNA is $tRNA^{Ala}$.

11. The system of claim 5 wherein said enzymatic cleavage site is recognized and cleaved by an enzyme selected from the group consisting of subtilisin, H64A subtilisin, Generase I, tobacco etch virus (TEV) protease, thrombin, factor Xa, and enterokinase.

* * * * *